United States Patent [19]

Archibald

[11] 4,277,226

[45] Jul. 7, 1981

[54] IV PUMP WITH EMPTY SUPPLY RESERVOIR AND OCCLUSION DETECTOR

[75] Inventor: G. Kent Archibald, White Bear Lake, Minn.

[73] Assignee: Avi, Inc., St. Paul, Minn.

[21] Appl. No.: 77,677

[22] Filed: Sep. 21, 1979

Related U.S. Application Data

[63] Continuation-in-part of Ser. No. 19,223, Mar. 9, 1979, Pat. No. 4,236,880.

[51] Int. Cl.³ .................... A61M 5/14; F04B 49/02
[52] U.S. Cl. .................................. 417/38; 417/63; 128/214 E; 128/214 F; 128/DIG. 12; 128/DIG. 13
[58] Field of Search ........ 128/214 E, 214 F, DIG. 12, 128/DIG. 13; 417/36, 38, 44, 63, 478; 73/168; 222/55, 214

[56] References Cited

U.S. PATENT DOCUMENTS

| | | | |
|---|---|---|---|
| 1,744,684 | 1/1930 | Griffith | 417/44 |
| 2,412,397 | 12/1946 | Harper | 417/478 |
| 3,048,121 | 8/1962 | Sheesley | 417/478 |
| 3,518,033 | 6/1970 | Anderson | 417/478 |
| 3,799,702 | 3/1974 | Weishaar | 417/38 |
| 3,855,515 | 12/1974 | Hutchins, Jr. | 318/685 |
| 4,042,153 | 8/1977 | Callahan et al. | 222/207 |
| 4,080,966 | 3/1978 | McNally et al. | 128/214 E |

*Primary Examiner*—Charles N. Hart
*Assistant Examiner*—David R. Sadowski
*Attorney, Agent, or Firm*—Kinney, Lange, Braddock, Westman and Fairbairn

[57] ABSTRACT

A volumetric infusion pump useful in intravenous feeding includes a detector which provides an alarm when the supply bag or reservoir becomes empty or an occlusion occurs between the supply bag and the pump. The pump includes a first pumping chamber having a cylinder, a piston, a first flexible diaphragm and first and second valves. The piston is driven by a first cam through a first cam follower which is connected to the piston. The empty supply bag detector senses contact between the first cam and the first cam follower. During normal operation, when the first valve opens and the second valve closes the first pumping chamber fills due to the head pressure of fluid from the bag, and the cam follower remains in contact with the cam. When the supply bag becomes empty due to an improper setup or a system malfunction such as an occlusion occurs, head pressure in the fluid being supplied to the pumping chamber is lost, and the cam follower no longer can maintain contact with the cam during the fill portion of the pumping cycle. This results in an alarm signal which stops the pump.

13 Claims, 1 Drawing Figure

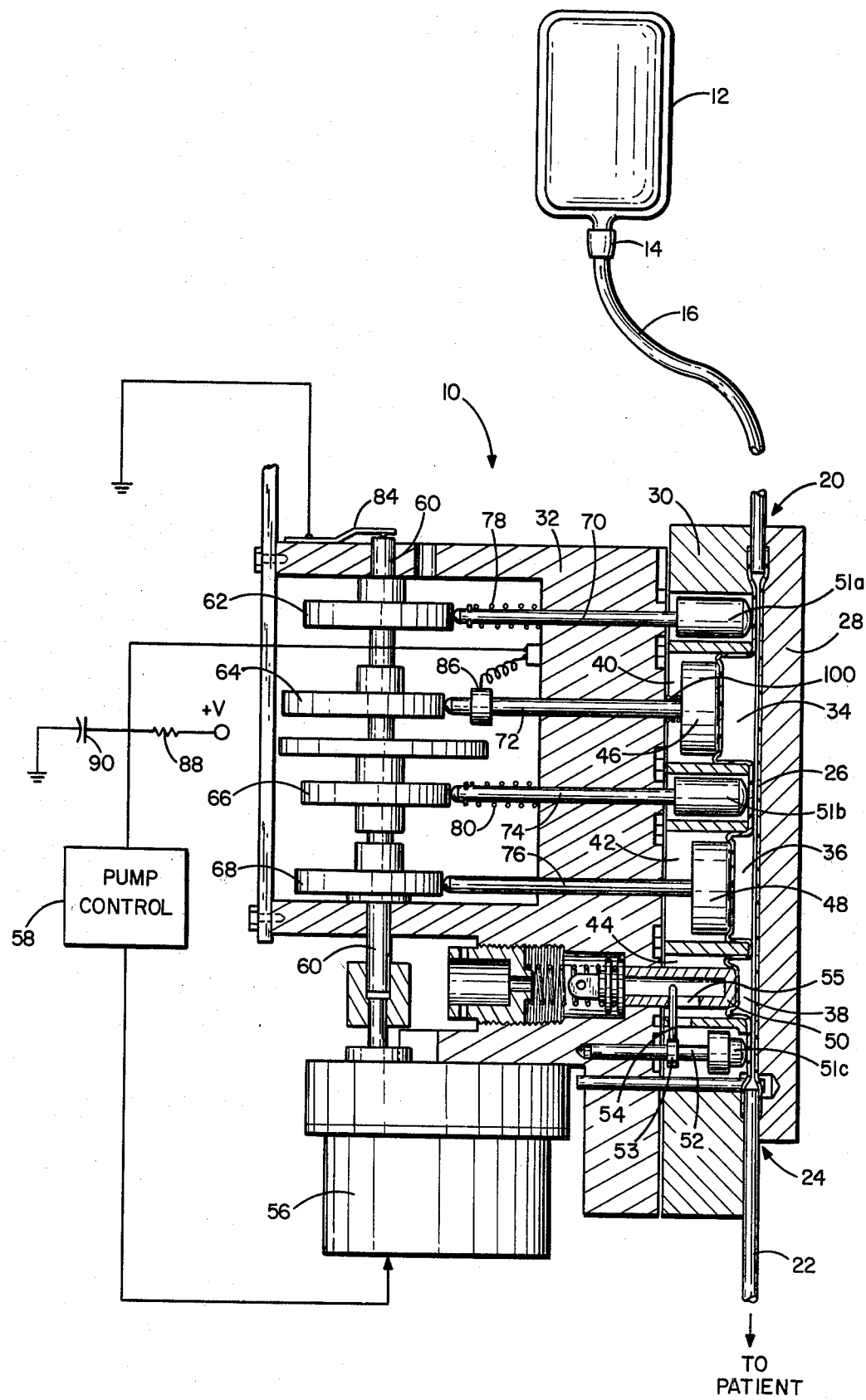

IV PUMP WITH EMPTY SUPPLY RESERVOIR AND OCCLUSION DETECTOR

REFERENCE TO CO-PENDING APPLICATION

The present application is a continuation-in-part of my previously filed U.S. patent application Ser. No. 19,223 filed Mar. 9, 1979, now U.S. Pat. No. 4,236,880, and assigned to the same assignee as the present application.

BACKGROUND OF THE INVENTION

1. Field of the Invention

The present invention relates to pumping apparatus. In particular, the present invention relates to an empty supply bag detector for use with volumetric infusion pumps for administration of intravenous (IV) fluids.

2. Description of the Prior Art

To improve health care, there has been considerable effort with regard to the administration of intravenous (IV) fluid. For many years IV solutions were administered only by the force of gravity. The volume rate was measured by counting the number of drops per minute. In many instances this method proved unsatisfactory. Drop size is directly proportional to surface tension, which is affected by viscosity, temperature, type of solution, and also drop size is affected by the speed at which the drop forms. The drop rate is affected by the gravitational force and the restrictions of the tube and needle. If a tube is partly occluded, the drop rate will decrease or as the IV supply decreases the hydrostatic pressure will decrease causing a decrease in drop rate. In many cases, therefore, the variability of both the drop size and the drop rate (both of which are for the most part beyond the control of the operator) makes this method of administration of intravenous fluid unsatisfactory.

Improvements have been made by adding an electronic drop counter together with either a controller or a peristaltic pump. The electronic drop counter and controller combination controls the drop rate but makes no improvements in controlling drop size, and also has the deficiency of not being able to control drop rate if back pressure increases beyond the hydrostatic forcing pressure. The electronic drop counter and peristaltic pump combination increases the forcing pressure but lacks an accurate metering method.

Improvement in metering methods results with the use of displacement pumps, which offer the capability of greater precision in controlling IV flow rates than is possible with the prior art IV controllers which depend on gravity. These pumps, in addition to metering the fluid, also apply positive pressure to the fluid or the IV tubing.

It has been recognized in the prior art that a dangerous condition can occur with volumetric infusion pumps if the supply bag or reservoir becomes empty while the pump continues to operate. The supply bag may become empty due to an improper setup by the medical personnel, or due to a system malfunction during operation of the pump. In either case, it is highly desirable to detect this condition and to stop the operation of the pump.

Several methods have been used in the prior art to detect an empty supply bag. In one system, a drop counter is placed on the drip chamber which is connected to the supply bag. When the bag goes empty, the drops cease, thereby providing an indication of the empty supply bag. This type of system, however, requires that the attending medical personnel connect a drop sensor to the drip chamber. This is a procedure in which setup problems can arise because of water level in the drip chamber, drops splashing, and ambient light.

A second system for detecting an empty supply bag places an air detector in the pump housing. This method, however, typically does not allow for easy removal of air from the pump housing. This leads to complications when a supply bag goes empty and must be replaced by a new bag. The air within the pump must be removed before operation of the pump can again be commenced.

A third system for detecting an empty supply bag includes a pump which detects an occlusion in the supply line between the supply bag and the pump in conjunction with a floating valve located in the drip chamber. This system has the disadvantage that it requires the extra expense of a floating valve in the drip chamber. Since the drip chamber must be part of the disposable portion of the system, the overall cost of the pumping system is increased.

There is a continuing need for a low cost, yet effective pump and empty supply bag detector which is simple to use, permits easy removal of air from the pump when supply bags have changed, and does not increase the cost of the disposable portions of the pumping system.

SUMMARY OF THE INVENTION

The volumetric infusion pump of the present invention provides simple, yet reliable detecting of an empty supply bag or reservoir. The present invention also detects an occlusion that may occur between supply bag and pump. The pump includes an inlet, an outlet, at least a first pumping chamber, and means for sensing head pressure of fluid being supplied to the pump inlet and the first cylinder. When head pressure decreases below a predetermined level, an alarm condition results and the pump is stopped.

In preferred embodiments, the first pumping chamber includes a first cylinder, a first piston, and first flexible diaphragm means. The first piston is driven by a first cam through a first cam follower which is connected to the first piston. During a fill portion of each pumping cycle a first valve between the inlet and the first pumping chamber opens and a second valve between the first pumping chamber and the outlet closes, to permit the first pumping chamber to be filled with fluid from the supply bag. The contact of the first cam and first cam follower during the fill portion of the cycle is maintained by the force of fluid within the first pumping chamber. In the case of an improper setup of the system or a system malfunction resulting in an empty supply bag or an occlusion between the supply bag and the pump inlet, head pressure is lost and the first cam follower cannot maintain contact with the first cam. This loss of contact between the cam and cam follower is sensed, and results in an alarm condition which stops the pump.

The cam and cam follower preferably are electrically conductive, and the contact between the first cam and first cam follower is sensed electrically. An integrated electrical signal is provided which is a function of the time period in which the cam and cam follower are not in physical, and therefore electrical, contact.

BRIEF DESCRIPTION OF THE DRAWINGS

The FIGURE shows a sectional, partially schematic view of an intravenous pump including the empty supply bag and occlusion detector of the present invention.

DETAILED DESCRIPTION OF THE PREFERRED EMBODIMENTS

The FIGURE illustrates the present invention, which includes an IV pump 10 of the general type described in my copending application Ser. No. 19,223. A detailed description of pump 10 is contained in that co-pending application, and a detailed description of the entire pump and its operation will not be repeated.

In the FIGURE, a supply bag or reservoir 12 containing IV fluid is connected to drop chamber 14, which in turn is connected by tubing 16 to inlet 20 of pump 10. Outlet tubing 22 is connected to outlet 24 of pump 10, and terminates at a needle (not shown) which is inserted into the patient.

Pump 10 includes disposable pump chamber 26, which is connected at its inlet and outlet ends to tubing 16 and 22, respectively. Disposable pump chamber 26 is inserted within a pump housing which includes top cover 28, diaphragm enclosure 30, and cam housing 32.

Disposable pump chamber 26 contains three flexible rolling diaphragm chambers 34, 36 and 38. Chambers 34 and 36 are first and second pumping chambers, respectively, while chamber 38 is a pressure monitoring chamber which moves in response to back pressure on fluid passing from chamber 26 through outlet tubing 22.

Diaphragm enclosure 30 includes first, second and third cylinders 40, 42 and 44 which receive rolling diaphragm chambers 34, 36 and 38, respectively. First piston 46 is movable within first cylinder 40 to vary the volume of first pumping chamber 34. Similarly second piston 48 is movable within second cylinder 42 to vary the volume of second pumping chamber 36. Both first piston 46 and second piston 48 are motor driven, as will be discussed later.

Unlike first and second pistons 46 and 48, third piston 50 is not motor driven, but rather is movable within third cylinder 44 in response to the fluid pressure within pressure sensing chamber 38. The operation of the back pressure sensor formed by third chamber 38, third cylinder 44 and third piston 50 is described in detail in my previously mentioned co-pending application.

First and second valves 51a and 51b are also provided within diaphragm enclosure 30. First valve 51a is positioned between inlet 20 and first pumping chamber 34. First valve 51a is motor driven, and when in its uppermost position, pinches off the flexible portion of disposable pumping chamber 10 between inlet 20 and first pumping chamber 34. When in its lowermost position first valve 51a permits fluid flow from inlet tubing 16 to first pumping chamber 34.

Similarly, second valve 51b is positioned between first and second pumping chambers 34 and 36. Second valve 51b is also motor driven, and when in its uppermost position, pinches off the flexible portion of disposable pumping chamber 26 between first pumping chamber 34 and second pumping chamber 36. When in its lowermost position, second valve 51b permits fluid flow from the first pumping chamber 34 to the second pumping chamber 36.

Also shown in the FIGURE is third valve 51c which is attached to shaft 52 and is linked through collar 53 and arm 54 to slot 55 in third piston 50. When pressure in third chamber 38 reaches a low level, the lower end of slot 55 engages arm 54 and forces third valve 51c against the flexible portion of disposable chamber 26 between third chamber 38 and outlet 24. Valve 51c, therefore, causes a slight back pressure within chambers 34, 36 and 38 which prevents the chambers from collapsing. At higher back pressures third piston 50 moves downward so that arm 54 no longer engages the bottom of slot 55 and third valve 51c is no longer forced against the portion of disposable chamber 26 between third chamber 38 and outlet 24. In my previously-mentioned co-pending application this same function is performed by a leaf spring which applies a slight force to the top half of the disposable chamber. Further description of the operation of valve 51c is contained in my co-pending application Ser. No. 077,620, filed on even date with this application.

Supported on cam housing 32 is motor 56, which is preferably a stepper motor. Motor 56 is controlled by pump control 58, which preferably includes a microcomputer control circuit (not shown). Pump control 58 controls the speed of motor 56, and when an alarm condition is sensed, pump control 58 causes motor 56 to stop, thereby terminating the operation of the pump, or causes the pump to operate at some other rate.

Motor 56 drives cam shaft 60 with attached cams 62, 64, 66 and 68. Cam 62 drives first valve 51a through cam follower rod 70, which has its lower end rounded to ride on cam 62 and which is attached at its upper end to first valve 51a.

Cam 64 drives first piston 46 through cam follower rod 72. The lower end of rod 72 rides on cam 64, while the upper end is threaded to permit attachment to first piston 46.

Second valve 51b is driven by cam 66 through cam follower rod 74, which is rounded at its lower end to ride on cam 66. The upper end of rod 74 is attached to second valve 51b.

Cam 68 drives second piston 48 by means of cam follower rod 76. The lower end of rod 76 is rounded to ride upon the surface of cam 68, and the upper end of rod 76 is threaded for connection to second piston 48.

Cam follower rods 70 and 74 have small springs 78 and 80 to urge the ends of rods 70 and 74, respectively against their respective cams 62 and 66.

Unlike rods 70 and 74, cam follower rods 72 and 76 are not spring biased against cams 64 and 68, respectively. Cam follower rod 72 and cam 64 provide the sensing mechanism. Cam follower rod 72 will follow cam 64 during the portion of the pumping cycle in which first pumping chamber 34 is being filled with IV fluid from bag 12 only if bag 12 is not empty and a head pressure is present. If no head pressure exists because bag 12 is empty or because of an occlusion in line 16 between bag 12 and pump 10, (or for any other reason) first chamber 34 will not expand to keep rod 72 in contact with cam 64. Optional spring 100 may be required to overcome compliance or memory of disposable chamber 26. Preferably the compliance of the material of disposable chamber 26 is such that with no or low head pressure rod 72 will not maintain contact with cam 64.

In the embodiment of the present invention shown in the FIGURE, the contact between cam 64 and cam follower rod 72 is monitored by a spring contact 84 which is in contact with metallic drive shaft 60, and a flexible contact 86 which is an electrical contact with cam follower rod 72. Spring contact 84 is connected to ground, while flexible contact 86 is connected to an integrating alarm circuit including resistor 88 and capacitor 90. As long as cam 64 and follower rod 72 remain in physical (and therefore electrical) contact, capacitor 90 is shorted through flexible contact 86, rod 72, cam 64, drive shaft 60 and spring contact 84. This is because rod 72, cam 64 and drive shaft 60 are all electrically conductive materials, preferably metal.

Because cam rod 72 may bounce or have intermittent contact with cam 64, even though there exists head pressure, it is desirable to integrate the alarm signal going to pump control 58. This integration is affected by resistor 88 and capacitor 90. The integration may be aided by sensing the position of cam 64 and discarding the alarm signal except when the point on cam 64 adjacent to rod 72 is decreasing in radius. This is the fill part of the cycle or the time when first valve 51a is in the down position.

In the event that the bag 12 becomes empty, or tube 16 is occluded the head pressure will be lost and during its fill portion of the cycle first chamber 34 will remain collapsed and will not force piston 46 and follower rod 72 toward cam 64. As a result, contact between rod 72 and cam 64 will be broken, and capacitor 90 will begin to charge through resistor 88, which is connected to a source of positive voltage (+V). If contact remains broken for a sufficient period of time for capacitor 90 to charge to a predetermined level, pump control 58 produces an alarm, which stops motor 56. In addition, the alarm may provide some visible or audible indication to the medical personnel of the existence of an empty bag condition, or an occlusion in the line between the bag and the pump.

During normal operation, first piston 46 and first valve 51a are initially at their uppermost position, and second piston 48 and second valve 51b are in their lowermost position. Second valve 51b then closes, and shortly thereafter first valve 51a moves downward to open. At this point, fluid from bag 12 is supplied through inlet tubing 16 and begins to fill first chamber 34. This drives piston 46 downward and maintains follower rod 72 in contact with cam 64. The downward movement of piston 46 draws additional fluid from supply bag 12, past open first valve 51a and into chamber 34 at a rate which is limited by the cam 64 surface.

At the same time first chamber 34 is filling, piston 48 is moving on an upstroke, thereby reducing the volume of second chamber 36 and pumping fluid from second chamber 36 through outlet tubing 22 to the patient.

When the first piston 46 reaches its lowermost position and second piston 48 is approaching its uppermost position, first valve 51a is driven upward to close fluid flow from supply bag 12 to first chamber 34. Second valve 51b is then moved downward to permit fluid flow from first chamber 34 to second chamber 36. After the two valves have been moved, piston 46 begins to move upward, thereby reducing the volume of first chamber 34, while second piston 48 moves downward, thereby increasing the volume of second chamber 36. The rate of decrease of the volume of first chamber 34 is preferably greater than the rate of increase of second chamber 36. As a result, some of the fluid being pumped from first chamber 34 is pumped out through outlet tubing 22 to the patient. By proper selection of the cross-sectional areas of chambers 34 and 36 and the rate of travel of pistons 46 and 48, the amount of fluid being pumped out through outlet tubing 22 may be essentially the same throughout the entire pumping cycle.

The empty bag sensing of the present invention occurs during each filling of first chamber 34, during which time first valve 51a is open and second valve 54 is closed so that fluid from supply bag 12 flows into first chamber 34. The lack of head pressure during this fill portion of the pumping cycle results in the alarm condition being created by the empty bag detector circuitry.

The need for the empty bag detector occurs in the case of an improper setup or a system malfunction. Under normal operating procedures the attending medical personnel sets up the pump for a particular volume limit which is less than the volume contained in supply bag 12. When the pump reaches this volume limit, pump control 58 stops motor 56, thereby stopping the pump 10 and produces an alarm which indicates to the medical personnel that action must be taken. If the volume limit is set improperly, and the supply bag 12 becomes empty, or some other malfunction occurs such as an occlusion, head pressure to first pumping chamber 34 when first valve 51a is open and second valve 51b is closed will be lost. In this case, cam 64 and cam follower 72 will not maintain contact, resulting in an alarm which stops motor 56.

With the present invention, the medical personnel can reset pump 10 after an empty bag alarm by simply hanging a new bag, clamping off tubing 22 to the patient, removing disposable pump chamber 26 from the pump housing, depressing the rolling diaphragms to cause any air to be forced upward back into supply bag 12, and replacing pumping chamber 26 in the pump housing. The needle does not have to be removed from the patient, nor is it required to remove air with a needle through the self-sealing diaphragm (not shown) which is provided in tubing 22 to inject drugs to the patient.

The pump of the present invention, therefore, has significant advantages over the prior art methods of detecting empty bags. First, the present invention does not require a drop counter, and therefore, setup problems in connecting a drop counter to drip chamber 14 are eliminated.

Second, the present invention permits easy removal of air from the pump by merely forcing the air back into bag 12. Removal of air is, of course, critical and it was a significant problem with some prior art pumps having empty bag detectors.

Third, the present invention senses an empty bag condition with a minimum of components. Unlike some prior art devices, a floating valve in drip chamber 14 is not required. This maintains the cost of the disposable portion of the pump at a minimum.

Fourth, the present invention permits an easy changeover of supply bags without requiring removal of the needle from the patient.

Fifth, the present invention may also eliminate the need for a drip chamber, since it is equally applicable to systems which simply have only a supply bag, and to systems having both a supply bag and a drip chamber.

Although the present invention has been described with reference to preferred embodiments, workers skilled in the art will recognize that changes may be made in form and detail without departing from the spirit and scope of the invention.

What is claimed is:

1. A volumetric infusion pump for pumping fluid from a reservoir to a patient, the volumetric infusion pump comprising:
   a pump inlet for connection to the reservoir;
   a pump outlet for connection to the patient;

a first pumping chamber connected between the pump inlet and the pump outlet, the first pumping chamber having a first cylinder, a first piston reciprocally movable in the first cylinder, and first flexible rolling diaphragm means between the first cylinder and the first piston, the first pumping chamber having a variable volume depending upon the position of the first piston in the first cylinder;

first cam means;

first cam follower means connected to the first piston and positioned to follow the first cam means;

first valve means between the pump inlet and the first pumping chamber for permitting fluid flow from the pump inlet to the first pumping chamber during a fill portion of each pumping cycle in which the first cam means permits movement of the first piston in a direction which increases the volume of the first pumping chamber;

second valve means between the first pumping chamber and the pump outlet for preventing fluid flow from the first pumping chamber to the pump outlet during the fill portion of each pumping cycle; and means for sensing contact between the first cam means and the first cam follower means and providing a signal indicative of whether the first cam follower means is in contact with the first cam means during the fill portion of each pumping cycle, a failure of the first cam follower means to maintain contact with the first cam means during the fill portion being indicative of a lack of fluid being supplied from the reservoir to the pump inlet.

2. The volumetric infusion pump of claim 1 and further comprising:

pump control means for controlling operation of the pump as a function of the signal indicative of whether the first cam follower means is in contact with the first cam means.

3. The volumetric infusion pump of claim 2 wherein the pump control means halts operation of the pump when the first cam follower means and the first cam means are out of contact for a predetermined time period.

4. The volumetric infusion pump of claim 3 wherein the means for sensing contact comprises:

first electrical contact means electrically connected to the first cam means;

second electrical contact means electrically connected to the first cam follower means;

integrating circuit means connected to the first and second electrical contact means for providing an integrated signal having a magnitude which is a function of time periods when the first cam means and the first cam follower means are not in contact.

5. The volumetric infusion pump of claim 4 wherein the pump control means halts operation of the pump when the magnitude of the integrated signal attains a predetermined value.

6. The volumetric infusion pump of claim 2 and further comprising:

motor means for driving the first cam means, the motor means being controlled by the pump control means.

7. A pump comprising:

a disposable pump chamber having an inlet, an outlet, and first and second flexible rolling diaphragm pumping chambers connected in a fluid flow passage between the inlet and the outlet wherein fluid is drawn into the first pumping chamber through the inlet;

a pump housing for receiving the disposable pump chamber;

a first cylinder in the housing positioned to receive the first flexible rolling diaphragm;

a second cylinder in the pump housing positioned to receive the second flexible rolling diaphragm;

a first piston movable in the first cylinder;

a second piston movable in the second cylinder;

first valve means for controlling fluid flow between the inlet and the first flexible rolling diaphragm pumping chamber;

second valve means for controlling fluid flow between the first flexible rolling diaphragm pumping chamber and the second flexible rolling diaphragm pumping chamber;

a motor;

a cam shaft driven by the motor, the cam shaft having first, second, third and fourth cams attached thereto;

first cam follower means connected to the first valve for following the first cam;

second cam follower means connected to the first piston for following the second cam;

third cam follower means connected to the second valve for following the third cam;

fourth cam follower means connected to the second piston for following the fourth cam; and means for sensing contact between the second cam and the second cam follower means wherein fluid pressure in the first pumping chamber urges the second cam follower means toward the second cam; and wherein failure of the second cam follower means to be in contact with the second cam when the first valve means is open, the second valve means is closed and the second cam has a radius which is decreasing is indicative of a lack of fluid being drawn into the first pumping chamber.

8. The pump of claim 7 and further comprising:

alarm means for providing an alarm signal when the second cam and the second cam follower means are out of contact for a predetermined time period.

9. The pump of claim 7 wherein spring means urges the first cam follower means into contact with the first cam.

10. The pump of claim 7 wherein the second cam follower means is urged toward the second cam solely by the first flexible diaphragm means and the fluid within the first flexible rolling diaphragm pumping chamber.

11. A volumetric infusion pump for pumping fluid from the reservoir to a patient, the volumetric infusion pump comprising:

a pump inlet for connection to the reservoir;

a pump outlet for connection to the patient;

a first pumping chamber connected between the pump inlet and the pump outlet;

first valve means between the pump inlet and the first pumping chamber;

second valve means between the first pumping chamber and the pump outlet;

valve control means for causing said first valve means to be closed and said second valve means to be open during a pump portion of each pumping cycle of said pump during which fluid is pumped from said pumping chamber, and for causing said first valve means to be open and said second valve means to be closed during a fill portion of each said pumping cycle during which said pumping chamber is filled by fluid from said pump inlet; and means for sensing position of a movable member which moves as a function of head pressure in the first pumping chamber during said fill portions of each said pumping cycle, wherein a head pressure below a predetermined level during said fill portion causes said movable member to have a position during said fill portion which indicates a lack of fluid being supplied from the reservoir to the pump inlet.

12. The volumetric infusion pump of claim 11 wherein the means for sensing head pressure provides an alarm signal when the head pressure is below the predetermined level.

13. The volumetric infusion pump of claim 12 and further comprising:

pump control means for controlling operation of the pump, wherein the pump control means controls operation of the pump in response to the alarm signal.

* * * * *